(12) United States Patent
Chen et al.

(10) Patent No.: US 9,714,728 B2
(45) Date of Patent: Jul. 25, 2017

(54) TUBE FITTING AND TUBE FITTING SET HAVING THE SAME

(71) Applicant: National Cheng Kung University, Tainan (TW)

(72) Inventors: Chao-Lin Chen, Tainan (TW); How-Ran Guo, Tainan (TW); Jin-Jia Hu, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 912 days.

(21) Appl. No.: 13/908,958

(22) Filed: Jun. 3, 2013

(65) Prior Publication Data

US 2014/0152000 A1 Jun. 5, 2014

(30) Foreign Application Priority Data

Dec. 3, 2012 (TW) .............................. 101145248 A

(51) Int. Cl.
| | |
|---|---|
| *F16L 3/237* | (2006.01) |
| *F16L 37/098* | (2006.01) |
| *F16L 41/02* | (2006.01) |
| *A61M 5/14* | (2006.01) |
| *A61M 39/10* | (2006.01) |

(52) U.S. Cl.
CPC ........... *F16L 3/237* (2013.01); *A61M 5/1418* (2013.01); *A61M 39/10* (2013.01); *F16L 37/098* (2013.01); *F16L 41/021* (2013.01); *A61M 39/1011* (2013.01); *A61M 2039/1027* (2013.01); *A61M 2039/1077* (2013.01)

(58) Field of Classification Search
CPC ................ A61M 39/10; A61M 5/1418; A61M 2039/1027; A61M 2039/1011; A61M 2039/1077; F16L 3/237; F16L 41/021; F16L 37/098; F16L 37/252; F16L 37/113; F16L 33/24
USPC ................. 285/188, 124.2, 133.11, 305, 921
See application file for complete search history.

(56) References Cited

U.S. PATENT DOCUMENTS

| | | | | |
|---|---|---|---|---|
| 3,521,332 A | * | 7/1970 | Kramer ..................... | F16B 2/22 248/229.26 |
| 3,572,375 A | * | 3/1971 | Rosenberg ............ | A61M 39/02 137/512 |
| 4,837,899 A | * | 6/1989 | Young ..................... | A47L 9/248 24/16 R |
| 5,464,257 A | * | 11/1995 | Riddles ................... | F16L 41/00 285/156 |

(Continued)

*Primary Examiner* — Gregory Binda
*Assistant Examiner* — Zachary Dragicevich
(74) *Attorney, Agent, or Firm* — DLA Piper LLP (US)

(57) ABSTRACT

A tube fitting includes a multi-way tube member and a coupler. The multi-way tube member includes three interconnected tube-connecting segments, one of which has two locking portions disposed at a distal end thereof. The coupler includes a cap section covering one of the tube-connecting segments having the locking portions, two resilient retaining portions snapped respectively to the locking portions, a guide tube section extending from the cap section into the one of the tube-connecting segments, and a connecting tube section extending from the cap section in a direction away from the guide tube section for connection with an additional coupler. A curable filler can be filled among the multi-way tube member, the coupler, and a tube for fixing the tube within the multi-way tube member.

5 Claims, 7 Drawing Sheets

(56) References Cited

U.S. PATENT DOCUMENTS

| | | | | |
|---|---|---|---|---|
| 6,298,525 | B1 * | 10/2001 | Margo | F16L 3/237 |
| | | | | 24/336 |
| 6,692,038 | B2 * | 2/2004 | Braun | F16L 37/1205 |
| | | | | 285/319 |
| 8,777,931 | B2 * | 7/2014 | Davis | A61M 39/10 |
| | | | | 285/332 |
| 2004/0154142 | A1 * | 8/2004 | Capra | F16L 23/08 |
| | | | | 24/278 |
| 2012/0174526 | A1 * | 7/2012 | Hsu | E04G 15/061 |
| | | | | 52/741.4 |
| 2013/0048826 | A1 * | 2/2013 | Go | E02F 9/2275 |
| | | | | 248/560 |
| 2014/0167412 | A1 * | 6/2014 | Magnone | F16L 37/256 |
| | | | | 285/403 |

\* cited by examiner under patent laws

TUBE FITTING AND TUBE FITTING SET HAVING THE SAME

CROSS-REFERENCE TO RELATED APPLICATION

This application claims priority of Taiwanese Application No. 101145248, filed on Dec. 3, 2012.

BACKGROUND OF THE INVENTION

1. Field of the Invention

This invention relates to a connecting member, and more particularly to a tube fitting.

2. Description of the Related Art

In a surgery operation, an animal experiment, or industry equipment, it is sometimes necessary to interconnect two tubes quickly by a tube fitting. A conventional tube fitting typically includes a tubular member and two flexible tubular tube-connecting members that are sleeved respectively on two open ends of the tubular member. This connecting manner, however, is not suitable for tubes delivering high-pressure fluid, e.g., of a fluid pressure greater than 10 kg/cm$^2$, or soft tubes due to possible removal of the tubes from the conventional tube fitting.

SUMMARY OF THE INVENTION

The object of this invention is to provide a tube fitting set that can interconnect effectively two tubes by pouring a curable filler between the tube fitting and the tubes.

According to an aspect of this invention, there is provided a tube fitting adapted to be connected to a tube, the tube fitting comprising:

a multi-way tube member including three tube-connecting segments in fluid communication with each other and each having a distal end formed with an end opening, the distal end of at least one of the tube-connecting segments having two locking portions and at least one overflow notch; and a coupler mounted removably to and in fluid communication with one of the tube-connecting segments having the locking portions and including a cap section covering the distal end of the one of the tube-connecting segments, two spaced-apart resilient retaining portions extending from the cap section and permitting the locking portions to be snapped respectively thereto so as to position the cap section relative to the one of the tube-connecting segments, a guide tube section that extends from the cap section into the one of the tube-connecting segments to guide the cap section to be sleeved on the distal end of the one of the tube-connecting segments and that is adapted to connect with one of the tubes extending into the one of the tube-connecting segments to retain the one of the tubes thereon, and a connecting tube section extending from the cap section in a direction away from the guide tube section and adapted for connection with an additional coupler, the cap section being formed with a connecting hole in spatial communication with the guide tube section and the connecting tube section.

According to another aspect of this invention, there is provided a tube fitting set comprising:

two multi-way tube members, each of the multi-way tube members including three tube-connecting segments in fluid communication with each other and each having a distal end formed with an end opening, the distal end of at least one of the tube-connecting segments of each of the multi-way tube members having two locking portions and at least one overflow notch; and two couplers each mounted removably to and in fluid communication with one of the tube-connecting segments of a corresponding one of the multi-way tube members having the locking portions and including a cap section covering the distal end of the one of the tube-connecting segments, two spaced-apart resilient retaining portions extending from the cap section and permitting the locking portions to be snapped respectively thereto so as to position the cap section relative to the one of the tube-connecting segments, a guide tube section that extends from the cap section into the one of the tube-connecting segments to guide the cap section to be sleeved on the distal end of the one of the tube-connecting segments and that is adapted to connect with one of the tubes extending into the one of the tube-connecting segments to retain the one of the tubes thereon, a connecting tube section extending from the cap section in a direction away from the guide tube section and adapted for connection with the other of the couplers, and a connecting hole formed through the cap section and in spatial communication with the guide tube section and the connecting tube section, the connecting tube section of one of the couplers having an internally threaded portion, the connecting tube section of the other of the couplers having an externally threaded portion engaging the internally threaded portion, so that the couplers are interconnected firmly.

According to still another aspect of this invention, there is provided a tube fitting set comprising:

two multi-way tube members, each of the multi-way tube members including three tube-connecting segments in fluid communication with each other and each having a distal end formed with an end opening, the distal end of at least one of the tube-connecting segments of each of the multi-way tube members having two locking portions and at least one overflow notch;

two couplers each mounted removably to and in fluid communication with one of the tube-connecting segments of a corresponding one of the multi-way tube members having the locking portions and including a cap section covering the distal end of the one of the tube-connecting segments, two spaced-apart resilient retaining portions extending from the cap section and permitting the locking portions to be snapped respectively thereto so as to position the cap section relative to the one of the tube-connecting segments, a guide tube section that extends from the cap section into the one of the tube-connecting segments to guide the cap section to be sleeved on the distal end of the one of the tube-connecting segments and that is adapted to connect with one of the tubes extending into the one of the tube-connecting segments to retain the one of the tubes thereon, a connecting tube section extending from the cap section in a direction away from the guide tube section and adapted for connection with the other of the couplers and in spatial communication with the guide tube section and the connecting tube section, the connecting tube section of one of the couplers having an internally threaded portion, the connecting tube section of the other of the couplers having an externally threaded portion engaging the internally threaded portion, so that the connecting tube sections of the couplers being interconnected removably; and at least one clamp disposed between and clamping removably the multi-way tube members.

BRIEF DESCRIPTION OF THE DRAWINGS

These and other features and advantages of this invention will become apparent in the following detailed description of the preferred embodiments of this invention, with reference to the accompanying drawings, in which.

DETAILED DESCRIPTION OF THE PREFERRED EMBODIMENTS

Figure 1:
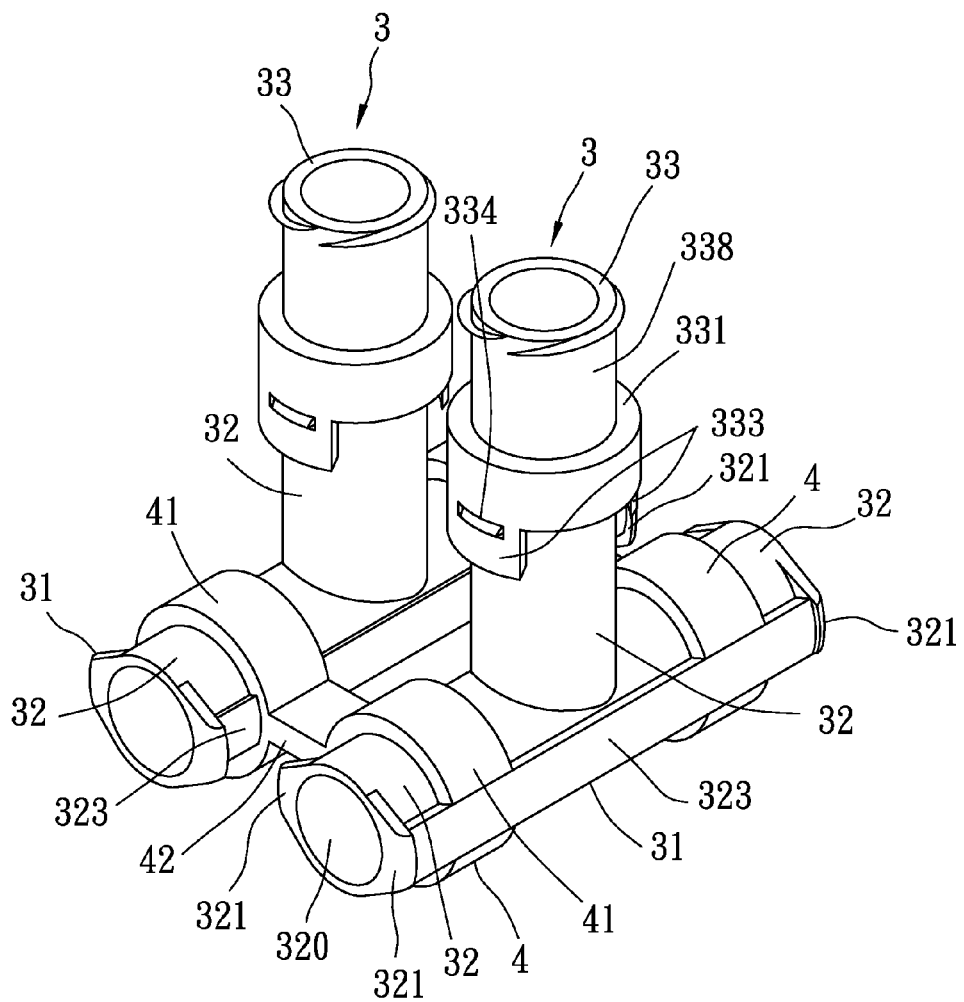
FIG. 1 is a perspective view of the first preferred embodiment of a tube fitting set according to this invention.

Before the present invention is described in greater detail in connection with the preferred embodiments, it should be noted that similar elements and structures are designated by like reference numerals throughout the entire disclosure.

Figure 2:
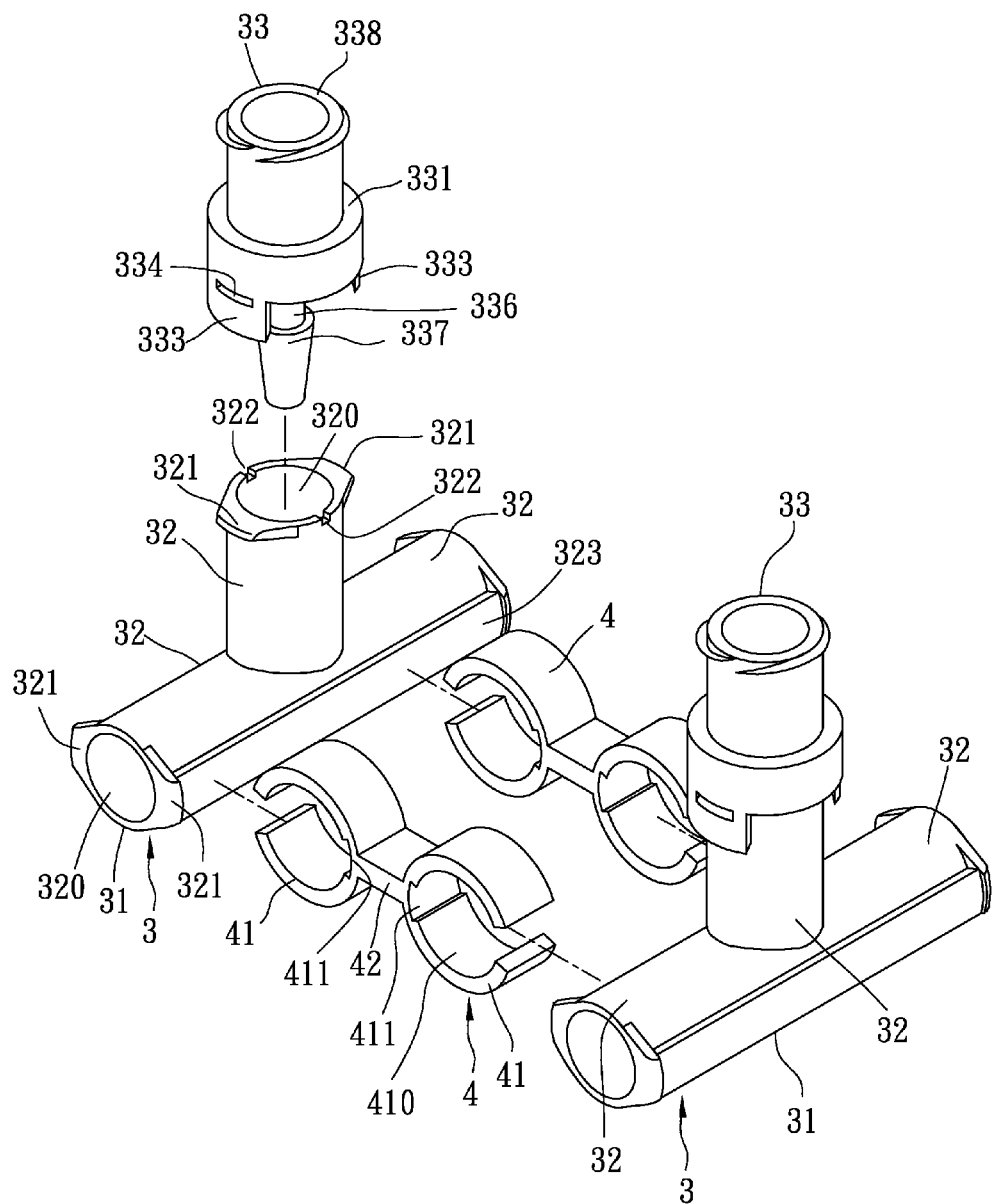
FIG. 2 is an exploded perspective view of the first preferred embodiment.
Figure 4:
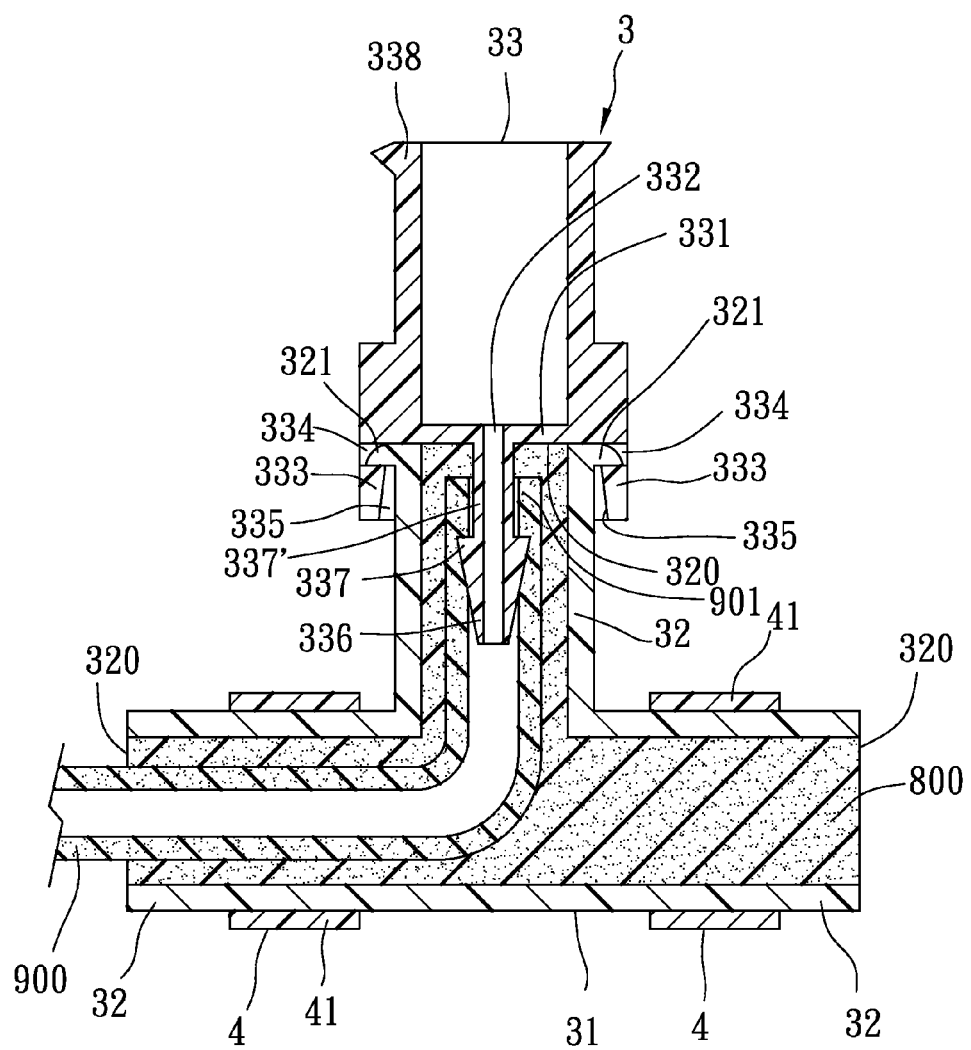
FIG. 4 is a sectional side view of the first preferred embodiment, illustrating that a curable filler is filled among a multi-way tube member, a coupler, and a tube.

Referring to FIGS. 1, 2, and 4, the first preferred embodiment of a tube fitting set according to this invention can be sleeved on two tubes 900 such that, when a curable filler 800 is poured and solidified between the tube fitting set and the tubes 900, the tube 900 is secured to the tube fitting. The filler 800 is but not limited to glue, thermoplastic resin, plastic steel, or other curable polymer material.

The tube fitting set includes two tube fittings 3 and two clamps 4 disposed between and connected removably to the tube fittings 3. The tube fittings 3 are connected respectively to the two tubes 900 so as to interconnect the two tubes 900.

Each of the tube fittings 3 includes a multi-way tube member 31 and a coupler 33 mounted removably to the multi-way tube member 31. Each multi-way tube member 31 includes three tube-connecting segments 32 in fluid communication with each other. Each of the tube-connecting segments 32 has an end opening 320. In this embodiment, the tube-connecting segments 32 are T-shaped. Two of the three tube-connecting segments 32 extend horizontally, and are aligned with each other along a left-to-right direction. The remaining tube-connecting segment 32 extends vertically, and is connected to a junction between the two horizontal tube-connecting segments 32. Alternatively, the multi-way tube member 31 may be of other three-prong shapes.

A distal end of each of the tube-connecting segments 32 has two diametrically opposed locking portions 321 configured respectively as two tongues extending radially away from each other. The distal end of the vertical tube-connecting segment 32 further has two diametrically opposed overflow notches 322 each disposed between the locking portions 321. Each multi-way tube member 31 has two axially extending anti-rotation projections 323 extending from outer surfaces of the two horizontal tube-connecting segments 32 away from each other.

Each coupler 33 is mounted removably to the corresponding vertical tube-connecting segment 32, and has a cap section 331 covering the end opening 320, two diametrically opposed resilient retaining portions 333 snapped respectively to the locking portions 321 and each configured as a flap and extending downwardly from the cap section 331, a guide tube section 336 coaxial with and extending downwardly from the cap section 331 into the corresponding tube-connecting segment 32, and a connecting tube section 338 extending upwardly from the cap section 331. The cap section 331 has a connecting hole 332 in fluid communication with the guide tube section 336 and the connecting tube section 338.

Each resilient retaining portion 333 has an engaging hole 334 formed therethrough and permitting the corresponding locking portion 321 to be snapped thereinto, and an inclined inner side surface 335 facing toward the corresponding tube-connecting segment 32 and spaced apart from the corresponding tube-connecting segment 32 by a distance that increases gradually in a direction away from the cap section 331 for guiding the distal end of the corresponding tube-connecting segment 32 into a space between the resilient retaining portions 333 to contact the cap section 331.

Each guide tube section 336 has a frustoconical head portion 337 at an end distal from the cap section 331 (i.e., lower end), and a neck portion 337' (see FIG. 4) disposed between the cap section 331 and the head portion 337.

The frustoconical head portion 337 has a diameter that reduces gradually in a direction away from the cap section 331.

Figure 3:
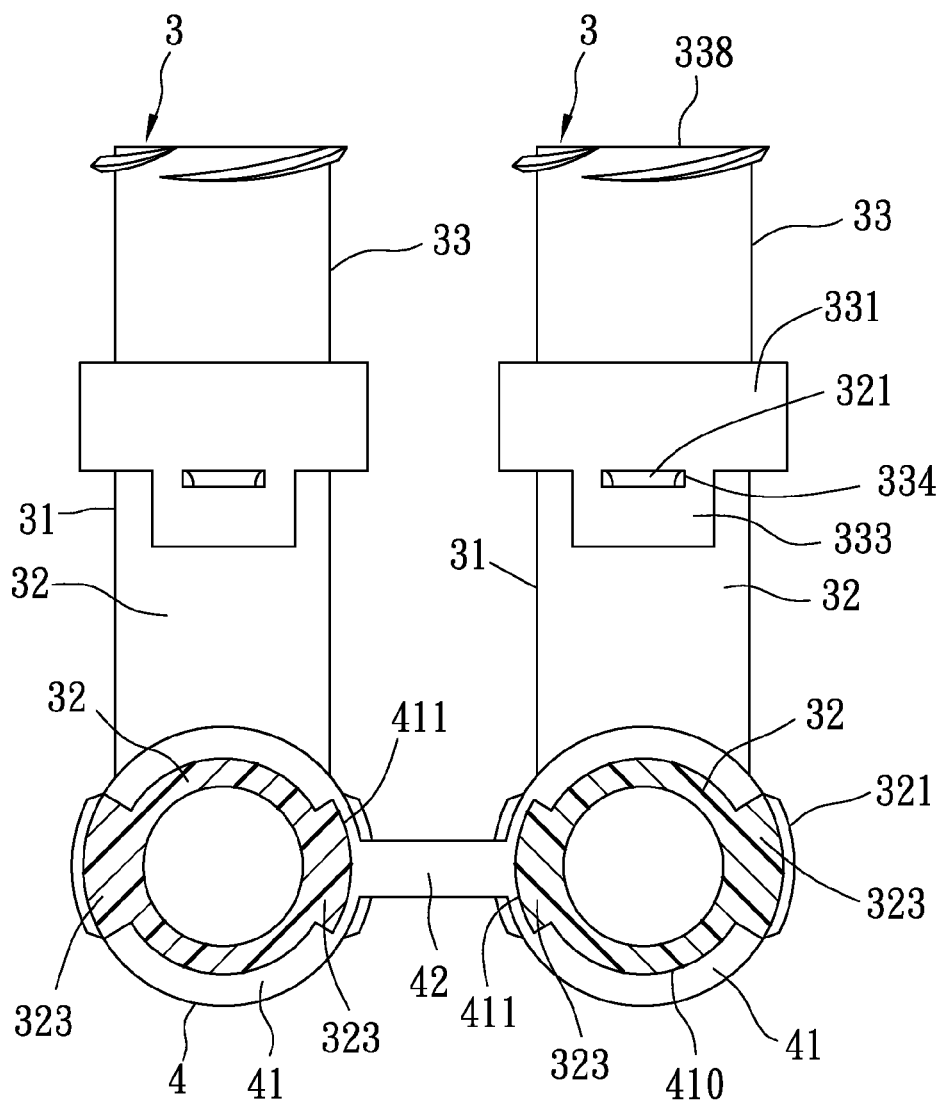
FIG. 3 is a sectional view of the first preferred embodiment.

With further reference to FIG. 3, each clamp 4 has two C-shaped clamping portions 41 each clamping removably the corresponding multi-way tube member 31, and a bridging portion 42 extending in a front-to-rear direction and connected between the C-shaped clamping portions 41. In this embodiment, each C-shaped clamping portion 41 clamps one horizontal tube-connecting segment 32, and has an abutment surface 410 abutting against an outer surface of the one horizontal tube-connecting segment 32 and formed with an engaging groove 411 that engages the one horizontal tube-connecting segment 32 of the one horizontal tube-connecting segment 32 for preventing rotation of the corresponding C-shaped clamping portion 41 relative to the one horizontal tube-connecting segment 32. In this embodiment, one of the two anti-rotation projections 323 of each horizontal tube-connecting segment 32 is engaged within the engaging groove 411 of the corresponding C-shaped clamping portion 41, and the other has two opposite side surfaces abutting respectively against two opposite end surfaces of the corresponding C-shaped clamping portion 41. The distance between the end surfaces of each C-shaped clamping portion 41 is equal approximately to the width of each anti-rotation projection 323 along a vertical direction, so as to allow for intimate contact between the end surfaces of the corresponding clamping portion 41 and the side surfaces of the corresponding anti-rotation projection 323.

With particular reference to FIG. 4, during use of the tube fitting set, one coupler 33 is assembled to one multi-way tube member 31, and an end of one tube 900 is inserted into the vertical tube-connecting segment 32 of the multi-way tube member 31 via the end opening 320 of one horizontal tube-connecting segment 32 to be sleeved on the guide tube section 336 of the coupler 33 such that an inwardly extending flange 901 is confined between the frustoconical head portion 337 and the cap section 331, thereby preventing removal of the tube 900 from the coupler 33.

Subsequently, the curable filler 800 is poured into the multi-way tube member 31 until it is filled among the multi-way tube member 31, the coupler 33, and the tube 900, such that air flows out of the multi-way tube member 31 via the overflow notches 322. After the curable filler 800 is solidified, the tube 900 is secured within the multi-way tube member 31. Afterwards, another tube 900 is secured within the other multi-way tube member 31 in the same manner. Finally, the clamps 4 are operated to clamp the two multi-way tube members 31.

Alternatively, the tube fitting set may include only one clamp 4. Or, both of the clamps 4 are omitted from the tube fitting set. In an alternative embodiment, additional anti-rotation projections may be formed on the vertical tube-connecting segment 32.

Figure 5:
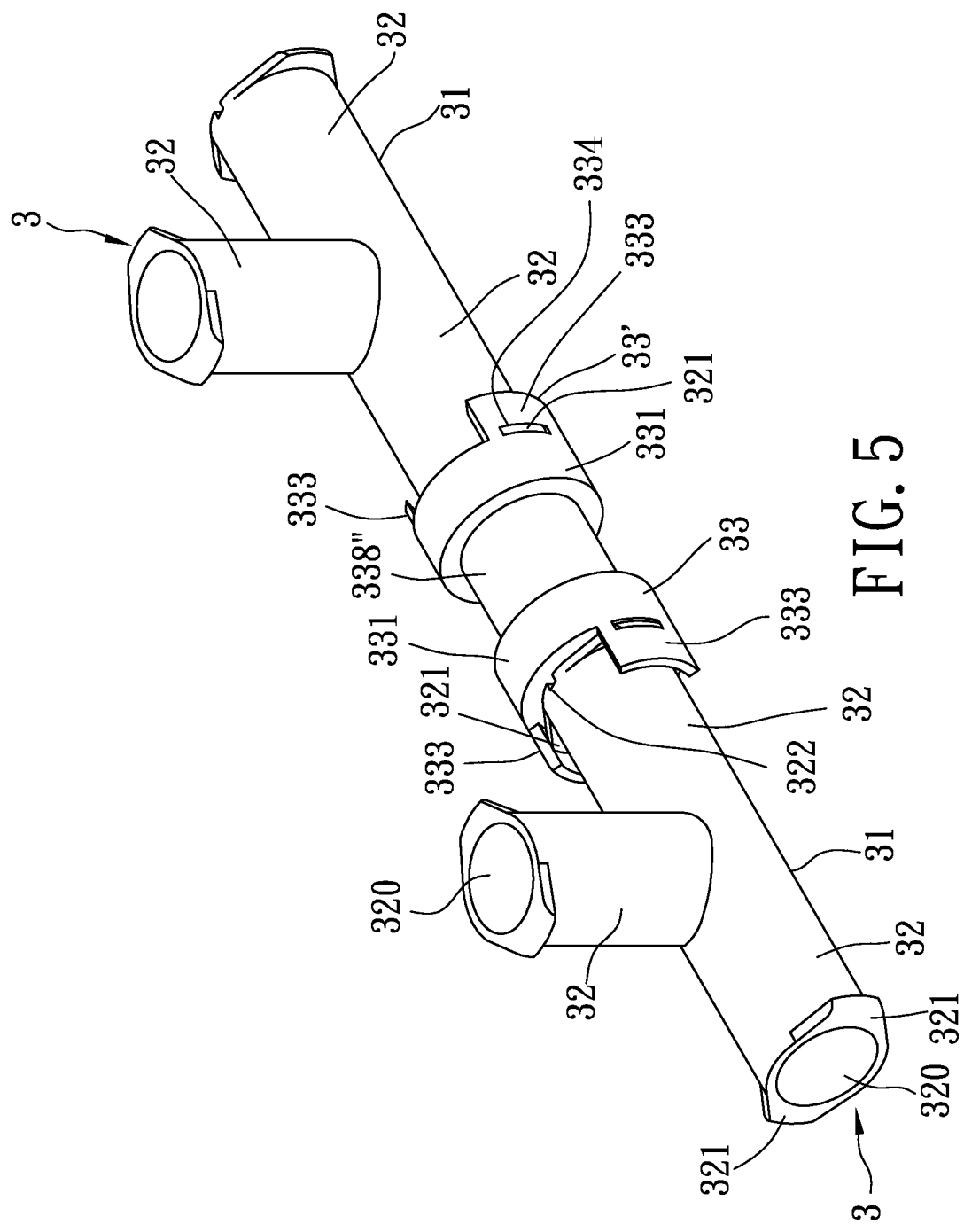
FIG. 5 is a perspective view of the second preferred embodiment of a tube fitting set according to this invention.
Figure 6:
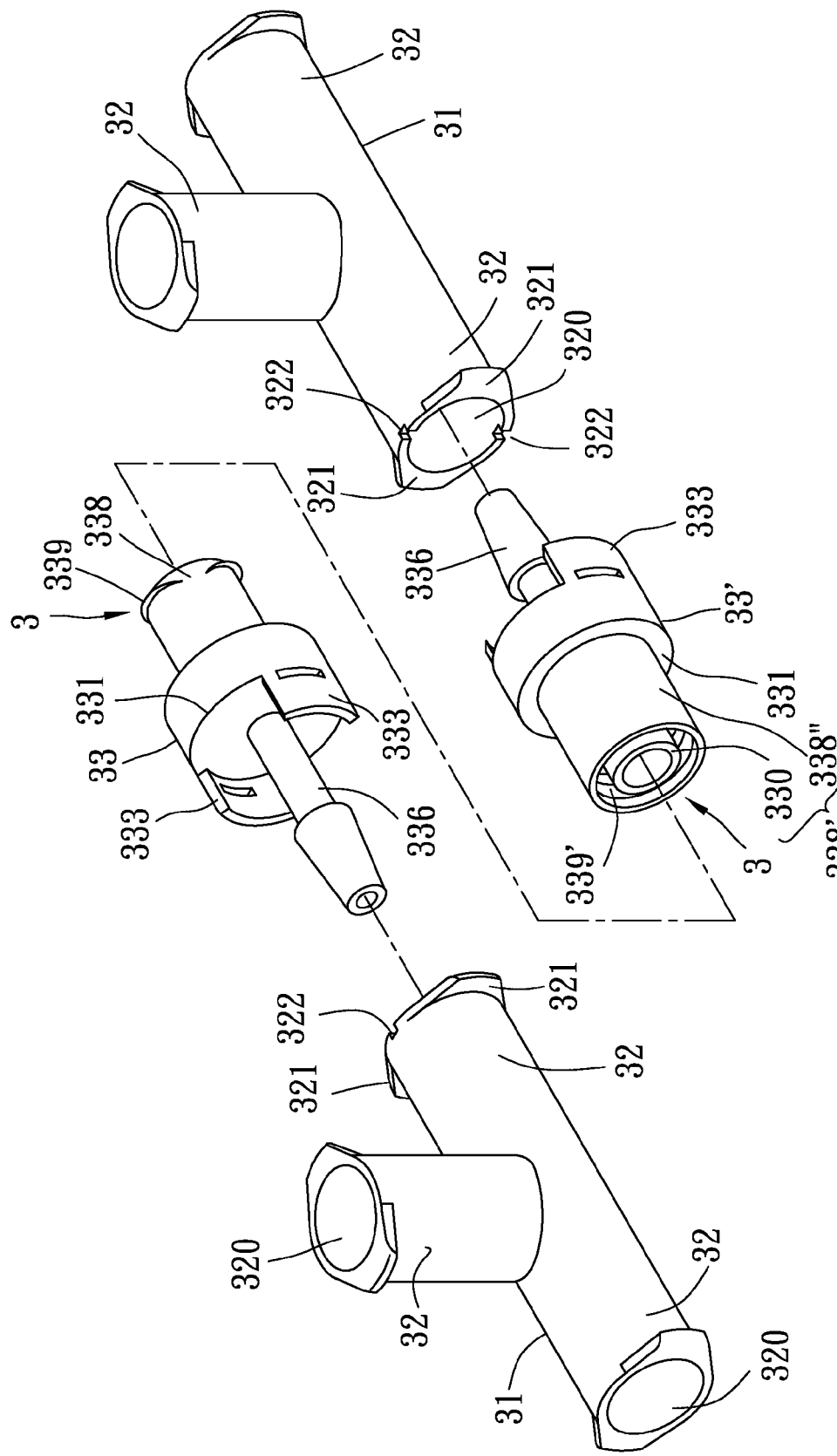
FIG. 6 is an exploded perspective view of the second preferred embodiment.
Figure 7:
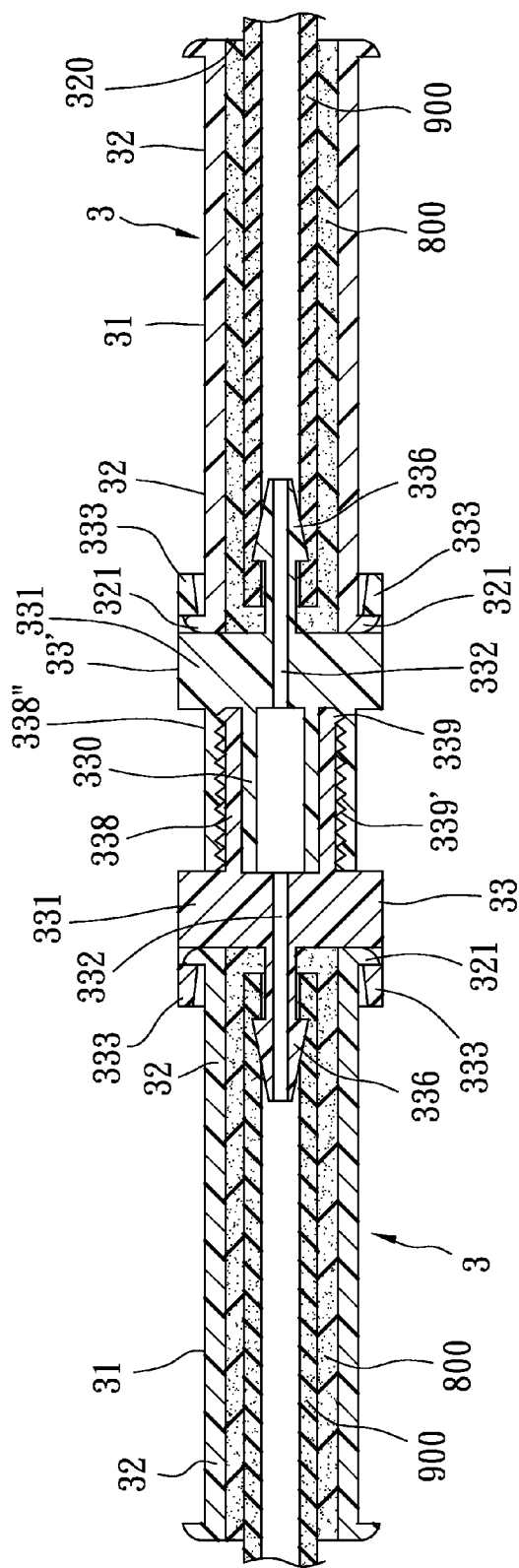
FIG. 7 is a sectional view of the second preferred embodiment, illustrating a threaded connection between two tube fittings.

FIGS. 5, 6, and 7 show the second preferred embodiment of a tube fitting set according to this invention, which is different from the first preferred embodiment in that the clamps 4 are omitted, and the structures of the multi-way tube members 31 and the couplers 33 are changed accordingly.

In this embodiment, the tube fitting set includes two tube fittings 3 each connected removably to a tube 900. The two tube fittings 3 are aligned, and are connected directly to and in fluid communication with each other so as to allow for fluid communication between the two tubes 900.

Unlike the first preferred embodiment, each overflow notch 322 is formed in one horizontal tube-connecting segment 32 instead of the vertical tube-connecting segment 32. The coupler 33 and a modified coupler 33' are mounted respectively to the horizontal tube-connecting segments 32. The connecting tube section 338' of the modified coupler 33' has an inner tubular portion 330 and an outer tubular portion 338" disposed around and spaced apart from the inner tubular portion 330 and having an internally threaded portion 339'. The connecting tube section 338 of the coupler 33 is inserted into a space between the inner and outer tubular portions 330, 338", and has an externally threaded portion 339 engaging the internally threaded portion 339'. The connecting hole 332 of each cap section 331 is disposed between and in fluid communication with the inner tubular portion 330 and the corresponding guide tube section 336.

During assembly, the guide tube section 336 of each of the coupler 33 and the modified coupler 33' is first inserted into one of the horizontal tube-connecting segments 32 of the corresponding multi-way tube member 31. Next, an end of each tube 900 is inserted into the other of the horizontal tube-connecting segments 32 of the corresponding multi-way tube member 31. Thereafter, the externally threaded portion 339 of the coupler 33 is engaged within the internally threaded portion 339' of the modified coupler 33'. Finally, the curable filler 800 is poured into the multi-way tube members 31 to fill spaces among the multi-way tube members 31, the coupler 33, the modified coupler 33', and the tubes 900, thereby preventing removal of the tubes 900 from the multi-way tube members 31.

When removal of the tube fittings 3 from each other is desired, it is only necessary to disengage the externally threaded portion 339 from the the internally threaded portion 339'.

To sum up, through cooperation of the couplers 33, 33' with the curable filler 800, the tubes 900 can be interconnected effectively, so that the tube fitting set of this invention is suitable for tubes delivering high-pressure fluid, thereby increasing the applicable range of the tube fitting set. Thus, the object of this invention is achieved.

With this invention thus explained, it is apparent that numerous modifications and variations can be made without departing from the scope and spirit of this invention. It is therefore intended that this invention be limited only as indicated by the appended claims.

We claim:

1. A tube fitting set comprising:
two multi-way tube members, each of said multi-way tube members including three tube-connecting segments in fluid communication with each other and each having a distal end formed with an end opening, said distal end of at least one of said tube-connecting segments of each of said multi-way tube members having two locking portions and at least one overflow notch;
two couplers each mounted removably to and in fluid communication with one of said tube-connecting segments of a corresponding one of said multi-way tube members having said locking portions and including a cap section covering said distal end of said one of said tube-connecting segments, two spaced-apart resilient retaining portions extending from said cap section and permitting said locking portions to be snapped respectively thereto so as to position said cap section relative to said one of said tube-connecting segments, a guide tube section that extends from said cap section into said one of said tube-connecting segments to guide said cap section to be sleeved on said distal end of said one of said tube-connecting segments and that is adapted to connect with one of the tubes extending into said one of said tube-connecting segments to retain said one of the tubes thereon, a connecting tube section extending from said cap section in a direction away from said guide tube section and adapted for connection with the other of said couplers, and a connecting hole formed through said cap section and in spatial communication with said guide tube section and said connecting tube section,; and
at least one clamp disposed between and clamping removably said multi-way tube members,
wherein said clamp has two C-shaped clamping portions and a bridging portion connected between said C-shaped clamping portions,
wherein at least one of said tube-connecting segments of each of said multi-way tube members has an outer surface formed with an axially extending anti-rotation projection, each of said C-shaped clamping portions having an abutment surface abutting against said outer surface of a corresponding one of said tube-connecting segments, said abutment surface being formed with an engaging groove that engages said anti-rotation projection of a corresponding one of said multi-way tube members for preventing rotation of a corresponding one of said C-shaped clamp portions relative to said corresponding one of said tube-connecting segments.

2. The tube fitting set as claimed in claim 1, wherein each of said resilient retaining portions of said couplers is configured as a flap extending from said cap section of a corresponding one of said couplers, and has an engaging hole formed therethrough, and each of said locking portions of said one of said tube-connecting segments of said multi-way tube members is configured as a tongue that extends from said distal end of said one of said tube-connecting segments and that is snapped into a respective one of said engaging holes of said resilient retaining portions.

3. The tube fitting set as claimed in claim 2, wherein each of said resilient retaining portions of said couplers further has an inclined inner side surface facing toward said one of said tube-connecting segments of a corresponding one of said multi-way tube members and spaced apart from said one of said tube-connecting segments of said corresponding one of said multi-way tube members by a distance that increases gradually in a direction away from said cap section of a corresponding one of said couplers for guiding said distal end of said one of said tube-connecting segments of said corresponding one of said multi-way tube members into a space between said resilient retaining portions of said corresponding one of said couplers to contact said cap section of said corresponding one of said couplers.

4. The tube fitting set as claimed in claim 1, wherein said guide tube section of each of said couplers has a frustoconical head portion at an end distal from said cap section, and a neck portion disposed between said cap section and said head portion, said frustoconical head portion having a diameter that reduces gradually in a direction away from said cap section.

5. The tube fitting set as claimed in claim 1, wherein said outer surface of said at least one of said tube-connecting segments is formed with two said anti-rotation projections, one of which is engaged within said engaging groove in a corresponding one of said C-shaped clamping portions and the other of which has two opposite side surfaces abutting respectively against two opposite end surfaces of said corresponding one of said C-shaped clamping portions.

* * * * *